United States Patent
Obiols et al.

(10) Patent No.: US 6,346,601 B1
(45) Date of Patent: Feb. 12, 2002

(54) PROCEDURE FOR OBTAINING THE SOMATOSTATIN ANALOG, OCTREOTIDE

(75) Inventors: Berta Ponsati Obiols; Gemma Jodas Farres; Marc Canas Poblet; Francisco Javier Clemente Rodriguez, all of Barcelona (ES)

(73) Assignee: Lipotec S.A., Barcelona (ES)

( * ) Notice: Subject to any disclaimer, the term of this patent is extended or adjusted under 35 U.S.C. 154(b) by 0 days.

(21) Appl. No.: 09/240,145

(22) Filed: Jan. 29, 1999

(30) Foreign Application Priority Data

Jan. 29, 1998 (ES) ................................. 9800162

(51) Int. Cl.$^7$ .......................... A61K 38/31; C07K 1/02; C07K 1/06; C07K 1/107
(52) U.S. Cl. ................... 530/311; 530/317; 530/328; 530/333; 530/335; 530/336; 530/338
(58) Field of Search ............................... 530/317, 328, 530/333, 335, 336, 338

(56) References Cited

U.S. PATENT DOCUMENTS 4,395,403 A   7/1983   Bauer et al.

FOREIGN PATENT DOCUMENTS

| EP | 029 579 A1 | 6/1981 |
| EP | 0 824 103 A | 2/1998 |

OTHER PUBLICATIONS

Osapay G. et al. J. Med. Chem., 40, 2241–2251, Jul. 1997.*
European Search Report Cover Sheet, including Annex.
Wu, Y–T, et al., Facile Solid Phase Synthesis of Octreotide Analogs Using P–Carboxybenzaldehyde as a Novel Linker to Anchor Fmos–Threoninol to Solid Phase Resins, Tetra. Ltrs., vol. 39, No. 13, pp. 1783–1784 (Mar. 1998).
Edwards, W.B., et al., "Generally Applicable, Convenient Solid–Phase Synthesis and Receptor Affinities of Octreotide Analogs," J. Med. Chem., vol. 37, pp. 3749–3757 (1994).
J. Press, "From Somatostatin to Sandostatin: History and Chemistry," Metabolism, vol. 41, No. 9, Suppl 2 (Sep.), 1992, pp. 5–6.
"Darstellung Geschutzter Peptide–Fragmente Under Einsatz Substituierter Triphenylmethyl–Harze," Tetrahedron Letters, vol. 30, No. 30, pp. 3943–3946 (1989).
"Veresterung Von Partiell Geschutzten Peptide–Fragmenten MIT Harzen. Einsatz Von 2–Chlortritlchlorid Zur Synthese Von Leu 15–Gastrin I," Tetrahedron Letters, vol. 30, No. 30, pp. 3947–3950 (1989).
W. Barry Edwards, et al., "Generally Applicable, Convenient Solid–Phase Synthesis and Receptor Affinities of Octreotide Analogs," J. Med. Chem., vol. 37, pp. 3749–3757 (1994).
W. Neugebauer, et al., "Solid–Phase Synthesis of C–Terminal Peptide Alcohols," Synthetic Methodologies and Peptide Bond Mimetics.
Jordi Alsina, et al., "Active Carbonate Resins for Solid–Phase Synthesis Through the Anchoring of a Hydroxyl Function. Synthesis of Cyclic and Alcohol Peptides," Tetrahedron Letters, vol. 38, No. 5, pp. 883–886 (1997).
M. Mergler, et al., "A New Acid–Labile Linker for the Solid–Phase Synthesis of Peptides with C–Terminal Threoninol," Poster Presentation 12th American Peptide Symposium, Jun. 6–21, 1991 (Boston).

* cited by examiner

*Primary Examiner*—M. Borin
(74) *Attorney, Agent, or Firm*—Bryan Cave LLP

(57) ABSTRACT

A procedure for obtaining the somatostatin analog, octreotide by means of solid phase synthesis on polymer supports and by intervention of protector groups of the Fmoc/tBu type. It includes construction of the seven amino acid, Boc-D-Phe-Cys(Trt)-Phe-D-Trp-Lys(Boc)Thr(tBu)-Cys(Trt)-Cl-trityl-R linear peptide, in which R is a polymer; treatment of the resulting peptidyl-resin with acid, for detachment of the peptide from the resin; cycling the linear structure obtained by reaction with iodine before or after incorporation of the threoninol residue into the terminal carboxy end; incorporating the threoninol residue in solution upon the seven amino acid protected peptide with or without the disulfide bridge formed; and removing the protections at the N-terminus and at the side chains with a treatment with 70–95% TFA in presence of scavengers to obtain octreotide.

8 Claims, No Drawings

PROCEDURE FOR OBTAINING THE SOMATOSTATIN ANALOG, OCTREOTIDE

FIELD OF THE INVENTION

This invention involves a procedure for preparation of the somatostatin analog, octreotide and its pharmaceutically acceptable salts formed by addition of acids or complexes of the same. Likewise, the invention is related to the preparation of intermediate compounds useful in the synthesis of octreotide in accordance with the invention.

BASIS OF THE INVENTION

While somatostatin possesses a very broad therapeutic potential and could be administered in a wide variety of clinical applications, its mean half-life in plasma is extremely short, reducing the number of applications possible. This drawback has promoted a number or research groups to establish the goal of developing more stable and more powerful analogs of somatostatin. One of these groups made a number of tests with cyclic octapeptides. One of these octapeptides yielded excellent biological activity both in vitro and in vivo (Pless J., Metabolism 41, 5–6 (1992)). This analog is Octreotide. Its structure is shown below:

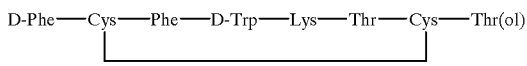

The presence of D-phenylalanine in the N-terminal end and an amino alcohol in the C-terminal end, along with the D-tryptophan residue and the disulfide bridge, make the molecule very resistant to metabolic degradation. The octreotide permits a 24 hour incubation in aggressive medium such as gastric juices or in intestinal mucosa.

Octreotide inhibits growth hormone for a lengthy period, inhibits the secretion of glucagon to a lesser degree, and inhibits insulin secretion only in a transient manner. It is thus more selective than other somatostatin analogues in regulating the levels of growth hormone in the body and therefore at present is indicated in acromegaly to control and reduce the plasma levels of such hormone. It is also used in the treatment of cellular alterations of gastroenteropancreatic endocrine origin and of certain types of tumors.

STATE OF THE ART

The primary ocreotide preparation described is a classic synthesis in solution (Bauer W., Pless J., (Sandoz) Eur. Pat. Appl. 29,579. Eidem U.S. Pat. No. 4,395,403 (1981, 1983). Syntheses in solid phase have been described subsequently (Mergler et al., Alsina et al., Neugebauer). In all of them, the objective is to form the entire peptide chain by solid phase peptide synthesis, starting the synthesis by the threoninol residue. This makes it mandatory to protect this residue.

The first author (Mergler M., Hellstern H., Wirth W., Langer W., Gysi P. and Prikoszovich W., Peltides: Chemistry and Biology; Proceedings of the 12th American Peptide Symposium. Smith, J. A. and Rivier J. E., Eds ESCOM, Leiden, Poster 292 Presentation (1991)) describes a synthetic process, using an aminomethyl resin upon which the Threoninol residue is incorporated with the two alcohol functions protected in acetal form. They carry out the synthesis following an Fmoc/tBu protection scheme, forming the disulfide bridge on resin by oxidation of the thiol groups of the previously deprotected cysteine residues and releasing and deprotecting the peptide with a 20% mixture of TFA/DCM.

In early 1997, Alsina J. et al. (Alsina J., Chiva C., Ortiz M., Rabanal F., Giralt E. and Albericio F., Tetrahedron Letters 38, 883–886 (1997)) described the incorporation, on active carbonate resins, of a Threoninol residue with the amino group protected by the Boc group and the side chain protected by a Bzl group. The synthesis was then continued by Boc/Bzl strategy. Formation of the disulfide bridge was carried out directly on resin using iodine, and the peptide was cleaved from the resin and its side chain protecting groups were simultaneously removed with HF/anisole 9/1. At a final stage the formyl group was removed with a piperidine/DMF solution. Neugebauer (Neugebauer W., Lefevre M. R., Laprise R., Escher E., Peptides: Chemistry, Structure and Biology, p. 1017, Marshal G. R. and Rivier J. E., Eds ESCOM, Leiden (1990)) described a linear synthesis with a yield of only 7%.

Edwards et al. (Edwards B. W., Fields C. G., Anderson C. J., Pajeau T. S., Welch M. J., Fields G. B., J. Med. Chem. 37 3749–3757 (1994)) carried out another solid-phase type approximation; they synthesized step-by-step on the resin, the peptide D-Phe-Cys(Acm)-Phe-D-Trp(Boc)-Lys(Boc)-Thr(tBu)-Cys(Acm)-HMP-resin. Next, they proceeded to form the disulfide on resin and then released the peptide from the resin by means of aminolysis with threoninol, with obtaining a total yield of only 14%.

All of these procedures carry out the formation of the disulfide bridge either on the totally deprotected peptide or on the resin.

SUMMARY OF THE INVENTION

This invention provides a procedure for obtaining octreotide and its pharmaceutically acceptable salts from acid addition, or complexes of same, by means of solid-phase synthesis upon polymer supports and with the intervention of protector groups of the Fmoc/tBu type, wherein it comprises the phases of:

1) Synthesis from the lineal peptide of seven amino acids

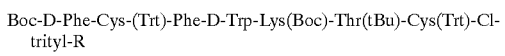

said peptide being suitably protected (wherein the cysteines are protected with the trityl group, the lysine with a Boc group and the threonine with a tBu group) and anchored upon a 2-chloro trityl-R type resin wherein R is a polymer insoluble in DCM and DMF, reticulated polystyrene and the like.

2) Selective cleavage of the peptide-resin link without affecting neither the protecting groups of the terminal amino end nor the side chain protecting groups for the trifunctional amino acids, or 3a) Activation of the terminal carboxy group of the protected peptide and incorporation of the threoninol residue with no type of activation; and 4a) Formation of the disulfide bridge by oxidation with iodine; or 3b) Formation of the disulfide bridge by oxidation with iodine; and 4b) Activation of the terminal carboxy group of the protected peptide, with the disulfide bridge already formed, and incorporation of the threoninol residue with no type of protection.

5) Deprotection of the lateral chains and of the terminal amino end and obtaining octreotide.

6) Purification of the crude ocreotide by preparatory HPLC.

The second method according to this invention is summarized by the following diagram:

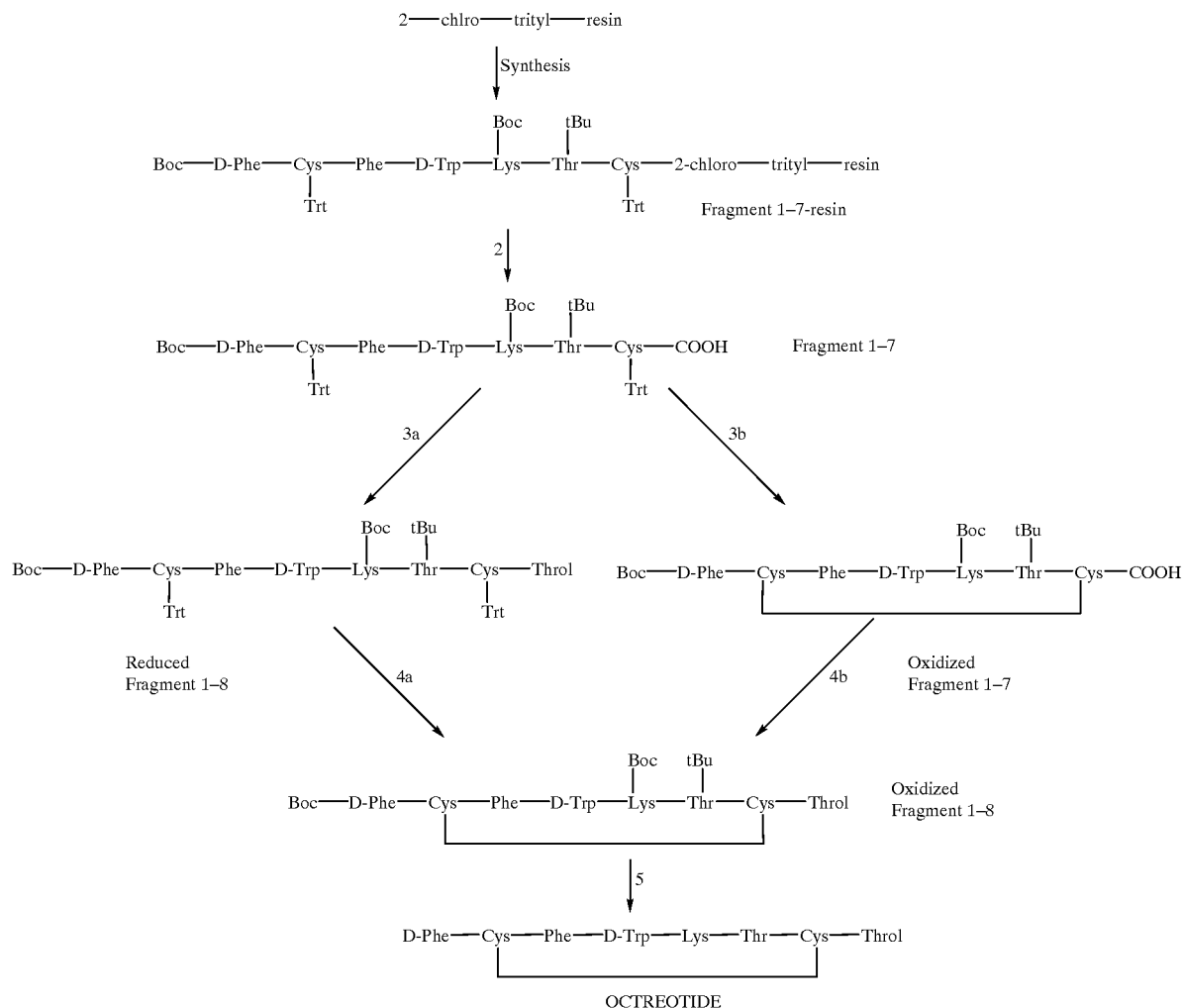

The basic difference from the other procedures already described is that the introduction of the threoninol is carried out upon the protected peptidic structure (resin-free), which, when appropriately activated, leads quantitatively and without needing to make temporary protections or derivations upon the threoninol, to the protected precursor of octreotide, which in turn, with a simple acid treatment leads to octreotide with very high yields.

DETAILED DESCRIPTION OF THE INVENTION

More specifically, this invention provides a procedure for obtaining octreotide based upon solid-phase synthesis with methodology of protecting groups of the type Fmoc/tBu upon a type-2-chloro trityl and the use of Boc-D-Phe for the terminal amino end of fragment 1-7 and subsequent incorporation of the threoninol residue as such.

The solid-phase synthesis is carried out using the 2-chloro trityl chloride resin (Barlos et al., *Tetrahedron Letters* 30, 3943–3946 (1989), Barlos et al., *Tetrahedron Letters* 30, 3947–3950 (1989)) incorporating in first place an Fmoc Cys (Trt). This support, due to its high steric hindrance, guarantees the incorporation of the Fmoc-Cys(Trt) residue without any racemization neither during the coupling itself nor during the subsequent basic treatments with 20% piperidine in DMF used to remove the Fmoc protecting group.

With the following peptidic skeleton (2-7) constructed:

Cys(Trt)-Phe-D-Trp-Lys-(Boc)-Thr(tBu)-Cys(Trt)-2-Cl-trityl-resin this invention adds Boc-D-Phenylalanine to the terminal-N end of the peptidic chain, to obtain the linear skeleton:

Boc-D-Phe-Cys(Trt)-D-Trp-Lys(Boc)-Thu(tBu)-Cys(Trt)-2-Cl-trityl-resin.

Subsequently, the peptide-resin is subjected to cleavage of the protected peptide fragment with acetic acide. The resulting product can either be cyclised by formation of a disulfide bridge with iodine in the same solution with simultaneous removal of the two trityl groups (3a), and subsequent incorporation of the threoninol residue (4a), or evaporated to a dry state to further proceed directly to the incorporation of the threoninol group by activation of the terminal carboxyl (3b) and subsequent oxidation of the entire peptide sequence.

The final step is always the removal of both the terminal amino protecting group of D-Phenylalanine (Boc) and the side chain protecting groups for Thr(t-Bu) and Lys(Boc) by means of a treatment with 70–95% TFA in presence of scavengers.

The crude octreotide is purified by HPLC and all of the homogeneous fractions are joined and lyophilized, thus obtaining octreotide in a 99% state of purity with a yield of the purification step of 60%.

Although it was at first expected that the activation of the C-terminal Cys residue required to couple the Threoninol would yield important amounts of (D-Cys)-octreotide, this reaction proceeded always with less than 1% epimerization. In short, this invention provides a procedure for obtaining octreotide, which is new and innovative in comparison with the synthetic strategies referring to already existing methods and described in the state of the art, with an overall synthesis and purification yield of greater than 40%.

The success of the invention lies in this feature which embodies a clear and competitive method for the synthesis of octreotide.

The abbreviations used in this description have the meanings set forth below:

| ACOH | acetic acid |
| Acm | acetamidomethyl |
| Boc | tert-butoxycarbonyl |
| Cys | L-cysteine |
| Cis | L-hemicysteine |
| D-Phe | D-phenylalanine |
| D-Trp | D-Tryptophan |
| DCM | dichloromethane |
| DIEA | N, N'-diisopropylethylamine |
| DIPCDI | diisopropylcarbodiimide |
| DMF | N, N-dimethylformamide |
| Fmoc | 9-Fluorenylmethoxycarbonyl |
| HMP-resin | hydroxymethylphenoxyacetyl-resin |
| HOBT | N-hydroxybenzotriazol |
| HPLC | high-performance liquid chromatography |
| Lys | L-Lysine |
| µL | microliters |
| µmol | micromoles |
| tBu | tert-butyl |
| TFA | trifluoroacetic acide |
| TFE | trifluoroethanol |
| Thr | L-threonine |
| Throl | L-threoninol |
| Trt | trityl |

The invention will be illustrated below with the following non-limitative examples:

EXAMPLE 1
Incorporation of the first amino acid. Obtaining of Fmoc Cys-Cl-trityl-resin.

The incorporation of the Fmoc-Cys(trt)-OH residue upon 2Cl-Trt resin is accomplished with an excess of 1 eq. of Fmoc Cys(Trt) and 2.5 eq. of DIEA.

2.93 g (5.0 mmol) of Fmoc-Cys(Trt) are incorporated upon 5 g of resin (f=1.28 mmol/g of resin, 6.4 mmol). The resin and the amino acid are weighed in separate containers and left to dry in a vacuum with KOH, for a minimum of two hours. A 1/1 solution of DIEA and DCM (dry on a 4A sieve) is prepared. The already dry amino acid is dissolved with dry DCM (on a 4A sieve) at a concentration of 0.1 g of resin per ml, adding the minimum quantity of dry DMF (on a 4A sieve) to complete the dissolution. One-third of the 1.8 ml (12.5 mmol) DIEA solution is added to this transparent solution in 1.8 ml of DCM. This is thoroughly homogenized and added to the dry resin. It is subjected to vigorous magnetic agitation for five minutes and the rest of the DIEA is added to the reaction; the mixture is allowed to react for forty minutes more. Then, 4 ml of dry MeOH are added and allowed to react for ten minutes, after which the resin is filtered on a filter plate with key, and the washings described below are carried out.

| Step | Reagent | Repetitions | Time |
| --- | --- | --- | --- |
| 1 | DMF | 3 | 1' |
| 2 | 5% piperidine (DMF/DCM) | 1 | 10' |
| 3 | 20% piperidine/DMF | 1 | 15' |
| 4 | DMF | 3 | 2' |

EXAMPLE 2
Incorporation of the different amino acids. Obtaining of Boc-D-Phe-Cys-(Trt)-D-Trp-Lys(Boc)-Thr(tBu)-Cys(Trt)-Cl-trityl-resin.

The incorporation of the amino acids is carried out following a synthesis program such as that described below, using an excess of 2.5 equivalents of Fmoc-amino acid, HOBt and DIPCDI. Later the Fmoc group is deprotected with 20% of piperidine/DMF for 1 min.+5 min.

| Step | Reagent | Repetitions | Time |
| --- | --- | --- | --- |
| 1* | DMF | 5 | 1' |
| 2* | pip/DMF 20% | 1 | 1' |
| 3* | pip/DMF 20% | 1 | 5' |
| 4* | DMF | 5 | 1' |
| 5* | Fmoc aa | — | + |
| 6 | HOBt | — | + |
| 7 | DIPCDI | — | 40' |
| 8 | DMF | 5 | –1' |

[*for Thr]

Control by Ninhydrin test; if +, return to 5; if – follow step 1 forward following amino acid.

The yields at the end of the synthesis are quantitative in obtaining Boc-D-Phe-Cys(Trt)-Phe-D-Trp-Lys (Boc)-Thr (tBu)-Cys(Trt)-2Cl-trityl-resin.

EXAMPLE 3
Preparation of Boc-D-Phe-Cys(Trt)-Phe-D-Lys(Boc)-Thr (tBu)-Cys(Trt)

250 mg (113 µmols) of Boc-D-Phe-Cys (Trt)-Phe-D-Trp-Lys (Boc)-Thr(tBu)-Cys(Trt)-2Cl-trityl-resin are treated with 6.36 ml of mixture 7/2/1 or 5.5/0.5/4 of DCM/TFE/AcOH, for two hours, under magnetic agitation. The suspension is then filtered and washed with 0.2 ml, 0.2 ml and 0.2 ml of the 7/2/1 mixture of DCM/TFE/AcOH. The solution is evaporated (if it is not desired to proceed with the oxidation) until dry, at reduced pressure, and the solid obtained is washed with water. The yield is quantitative.

EXAMPLE 4
Obtaining of cycle [(2-7)] Boc-D-Phe-Cis-Phe-D-Trp-Lys (Boc)-Thr(tBu)-Cis-OH (Oxidized 1-7 fragment).

250 mg (113 mmols) of Boc-D-Phe-Cys(Trt)-Phe-D-Trp-Lys(Boc)-Thr(tBu)-Cys(Trt)-COOH dissolved in 7 ml of the 7/2/1 mixture of DCM/TFE/AcOH, is slowly added to 290 mg (1.13 mmol) of iodine of 0.8 M concentration in the 7/2/1 mixture of DCM/TFE/AcOH. The reaction is allowed to evolve for 15 minutes. 4.3 ml of a $Na_2S_2O_7$, 1 N solution is added to eliminate the iodine excess. The aqueous phase is extracted and washed three times with 1 ml of DCM, the entirety of the organic phases is extracted with a citric acid/water solution and is evaporated at reduced pressure to dryness. The solid obtained is washed with the help of a filter plate and water. The yield fluctuates between 85 and 95%.

EXAMPLE 5

Coupling of cycle $^{(2-7)}$ Boc-D-Phe-Cis-Phe-D-Trp-Lys (Boc)-Thr(tBu)-Cis-OH (Oxidized 1-7 fragment) with Throl.

Over 250 mg (230 µmols) of $^{(2-7)}$ Boc-D-Phe-Cis-Phe-D-Trp-Lys(Boc)-Thr(tBu)-Cis-OH (Oxidized 1-7 fragment), 103 mg (690 µmol) of HOBt and 72 mg (690 µmol) of threoninol are weighed out and dissolved in 10 ml of dry DMF/dry DCM (1:1); under vigorous agitation, 111 µl (690 µmols) of DIPCDI are added. The mixture is allowed to react for five hours at room temperature. It is evaporated to dryness until an oil is obtained, water is added, the mixture is well homogenized by ultrasound and lyophilized. The coupling is quantitative.

EXAMPLE 6

Coupling of Boc-D-Phe-Cys(Trt)-Phe-D-Trp-Lys(Boc)-Thr (tBu)-Cys(Trt)-OH (Reduced fragment 1-7) with Throl.

Over 250 mg (149 µmol) of $^{(2-7)}$ Boc-D-Phe-Cis-Phe-D-Trp-Lys(Boc)-Thr(tBu)-Cis-OH (Oxidized 1-7 fragment), 67 mg (447 µmol) of HOBt and 47 mg (447 µmol) of threoninol are weighed out and dissolved in 10 ml of dry DMF/dry DCM (1:1), under vigorous agitation 70 µl [sic] (447 µmols) of DIPCDI are added. The mixture is allowed to react for five hours at room temperature. It is evaporated to dryness until an oil is obtained, water is added, the mixture is well homogenized by ultrasound, and lyophilized. The coupling is quantitative.

EXAMPLE 7

Coupling of cycle $^{(2-7)}$ Boc-D-Phe-Cis-Phe-D-Trp-Lys (Boc)-Thr(tBu)-Cis-OH (Oxidized 1-7 fragment) with the salt of HOBt of the preformed threoninol.

In this example, the same procedure as explained in Example 5 is followed, but in this case using salt of Hthrol$^+$ Obt$^-$ and DIPCDI, in dry DMF at a concentration of 25 mg/ml. The reaction is carried out at 47° C. The coupling is quantitative.

EXAMPLE 8

Coupling of cycle Boc-D-Phe-Cys(Trt)-Phe-D-Trp-Lys (Boc)-Thr(tBu)-Cys(Trt)-OH (Reduced 1-7 fragment) with the salt of HOBt of the preformed threoninol.

In this example, the same procedure as explained in Example 6 is followed, but in this case using the salt of Hthrol$^+$ Obt$^-$ and DIPCDI, in dry DMF at a concentration of 25 mg/ml. The reaction is carried out at 47° C. The coupling is quantitative.

EXAMPLE 9

Oxidation of Boc-D-Phe-Cys(Trt)-Phe-D-Trp-Lys(Boc)-Thr (tBu)-Cys(Trt)-Throl.
Obtaining of cycle $^{(2-7)}$ Boc-D-Phe-Cis-Phe-D-Trp-Lys (Boc)-Thr(tBu)-Cis-Throl (Oxidized fragment 1-8).

250 mg (147 µmols) of Boc-D-Phe-Cys(Trt)-Phe-D-Trp-Lys(Boc)-Thr(tBu)-Cys(Trt)-Throl dissolved in 8.26 ml of mixture 7/2/1 of DCM/TFE/AcOH, are slowly added to a solution of 290 mg (1.47 mmol) of iodine of 0.8 M concentration in the mixture 7/2/1 of DCM/TFE/AcOH. The reaction is allowed to evolve for 15 minutes. 4.3 ml of an Na$_2$S$_2$O$_7$ 1 N is added to eliminate the excess iodine. The aqueous phase is extracted and washed three times with 1 ml of DCM, the entirety of the organic phases is extracted with a solution of citric acid and water and is evaporated at reduced pressure to dryness. The solid obtained is washed with the help of a filter plate and water.

EXAMPLE 10

Removal of Protecting Groups. Obtention of Octreotide.

230 mmols cycle $^{(2-7)}$ Boc-D-Phe-Cis-Phe-D-Trp-Lys (Boc)-Thr(tBu)-Cis-Throl (Oxidized 1-8 fragment) obtained in Examples 5, 7 and 9 are treated with 2 ml of TFA/H$_2$O (95:5) for five hours at ambient temperature. Later, the filtrate is dropped over 100 ml of dry and cold diethyl ether and the white precipitate obtained is once again centrifuged. The solid is resuspended in diethyl either and centrifuged again, repeating the operation five times more. The crude peptide is purified by preparative HPLC at 25% of CH$_3$CN/H$_2$O with 0.01% TFA in a 10 µm

What is claimed:

1. A procedure for obtaining octreotide and its pharmaceutical acceptable salts comprising the steps of:

a) providing a linear peptide having the first sequence Boc-D-Phe-Cys(Trt)-Phe-D-Trp-Lys(Boc)-Thr(tBu)-Cys(Trt)-2Cl-trityl-R, wherein R is a polymer insoluble in dichloromethane or dimethylformamide;

b) treating the first sequence with an acid to obtain Boc-D-Phe-Cys(Trt)-Phe-D-Trp-Lys(Boc)-Thr(tBu)-Cys(Trt)OH;

c) obtaining (2,7 cyclic) Boc-D-Phe-Cys(Trt)-Phe-D-Trp-Lys(Boc)-Thr(tBu)-Cys(Trt)-Throl disulfide by:

1) oxidizing Boc-D-Phe-Cys(Trt)-Phe-D-Trp-Lys (Boc)-Thr(tBu)-Cys(Trt)OH in the presence of iodine to obtain(2,7 cyclic) Boc-D-Phe-Cys(Trt)-Phe-D-Trp-Lys(Boc)-Thr(tBu)-Cys(Trt)OH disulfide and contacting the latter with a threoninol residue, or 2) contacting Boc-D-Phe-Cys(Trt)-Phe-D-Tip-Lys (Boc)-Thr(tBu)-Cys(Trt)OH with a threoninol residue to obtain Boc-D-Phe-Cys(Trt)-Phe-D-Trp-Lys (Boc)-Thr(tBu)-Cys(Trt)-Throl and oxidizing Boc-D-Phe-Cys(Trt)-Phe-D-Trp-Lys(Boc)-Thr(tBu)-Cys (Trt)-Throl in the presence of iodine; and d) deprotecting side chains of (2,7 cyclic) Boc-D-Phe-Cys(Trt)-Phe-D-Trp-Lys(Boc)-Thr(tBu)-Cys(Trt)-Throl disulfide with 70–95% trifluoroacetic acid in the presence of scavengers to obtain (2,7 cyclic) D-Phe-Cys-Phe-D-Trp-Lys-Thr-Cys-Throl disulfide.

2. The method of claim 1, wherein the providing step (a) further comprises:

a) anchoring Fmoc-Cys(Tit)OH to Cl-trityl-R; and b) sequentially amidating with FmocThr(tBu)OH, FmocLys(Boc)OH, Fmoc-D-TrpOH, FmocPhe, FmocCys(Trt)OH, Boc-D-PheOH.

3. The method of claim 1, wherein the providing step (a) further comprises synthesizing the first sequence from amino residues by employing Fmoc as a temporary protector for the amino residues and wherein side chains of Cys are protected with Trityl groups, side chains of Lys are protected with Boc and side chains of Thr are protected with tBu.

4. The method of claim 1, wherein the treating step (b) further comprises treatment with a mixture of AcOH and one or more solvents selected from the group consisting of trifluoroethanol, methanol and dichloromethane.

5. The method of claim 1, wherein the obtaining step (c) of contacting of Boc-D-Phe-Cys(Trt)-Phe-D-Trp-Lys(Boc)-Thr(tBu)-Cys(Trt)OH with threoninol residue comprises activation of a C-terminal cysteine carboxyl group.

6. The method of claim 1, wherein the obtaining step (c) of contacting of Boc-D-Phe-Cys(Trt)-Phe-D-Trp-Lys(Boc)-Thr(tBu)-Cys(Trt)OH disulfide with threoninol residue comprises activation of a C-terminal cysteine carboxyl group with an active ester.

7. The method of claim 1, wherein, in the obtaining step (c), the oxidation of Boc-D-Phe-Cys(Trt)-Phe-D-Trp-Lys(Boc)-Thr(tBu)-Cys(Trt)OH is performed in a solution with iodine.

8. The method of claim 1, wherein, in the obtaining step (c), the oxidation of Boc-D-Phe-Cys(Trt)-Phe-D-Trp-Lys(Boc)-Thr(tBu)-Cys(Trt)-Throl is performed in a solution with iodine.

* * * * *

UNITED STATES PATENT AND TRADEMARK OFFICE
CERTIFICATE OF CORRECTION

PATENT NO. : 6,346,601 B1
DATED : February 12, 2002
INVENTOR(S) : Berta Ponsati Obiols et al.

It is certified that error appears in the above-identified patent and that said Letters Patent is hereby corrected as shown below:

<u>Column 8,</u>
Line 39, please change "Tip" to -- Trp --.

Signed and Sealed this

Second Day of July, 2002

Attest:

JAMES E. ROGAN
Attesting Officer  Director of the United States Patent and Trademark Office